United States Patent
Narayanan et al.

(10) Patent No.: US 6,664,120 B1
(45) Date of Patent: Dec. 16, 2003

(54) METHOD AND STRUCTURE FOR DETERMINING A CONCENTRATION PROFILE OF AN IMPURITY WITHIN A SEMICONDUCTOR LAYER

(75) Inventors: Sundar Narayanan, Santa Clara, CA (US); Krishnaswamy Ramkumar, San Jose, CA (US)

(73) Assignee: Cypress Semiconductor Corp., San Jose, CA (US)

( * ) Notice: Subject to any disclaimer, the term of this patent is extended or adjusted under 35 U.S.C. 154(b) by 0 days.

(21) Appl. No.: 10/023,065

(22) Filed: Dec. 17, 2001

(51) Int. Cl.$^7$ ............................................... H01L 21/66
(52) U.S. Cl. ........................................ 438/14; 257/48
(58) Field of Search ..................... 438/14, 16; 257/48

(56) References Cited

U.S. PATENT DOCUMENTS

| | | | | |
|---|---|---|---|---|
| 4,912,062 A | * | 3/1990 | Verma | 438/449 |
| 5,298,860 A | * | 3/1994 | Kato | 324/767 |
| 5,663,084 A | * | 9/1997 | Yi et al. | 438/453 |
| 5,712,208 A | * | 1/1998 | Tseng et al. | 438/770 |

FOREIGN PATENT DOCUMENTS

| | | | | |
|---|---|---|---|---|
| EP | 1 052 686 A2 | * | 11/2000 | H01L/21/265 |
| JP | 52-137275 | * | 11/1977 | H01L/21/76 |
| JP | 53-105369 A | * | 9/1978 | H01L/21/66 |
| JP | 11-233578 A | * | 8/1999 | G01N/21/00 |

OTHER PUBLICATIONS

IBM Technical Disclosure Bulletin, Jun. 1971, NN7106259, vol. 14, Issue No. 1, p. 259.*
Narayanan et al., "Monitoring Nitrogen Profiles in Ultrathin Gate Dielectrics," Electrochemical and Solid–State Letters, vol. 5, No. 7, 2002, pp. F15–F17.

* cited by examiner

Primary Examiner—Evan Pert
(74) Attorney, Agent, or Firm—Kevin L. Daffer; Conley Rose P.C.

(57) ABSTRACT

A method and a structure are provided for measuring a concentration of an impurity within a layer arranged upon a semiconductor substrate. The method may include exposing the layer and semiconductor substrate to oxidizing conditions and determining a difference in total dielectric thickness above the substrate from before to after exposing the layer and substrate. The difference may be correlated to a concentration of the impurity. In some cases, the method may include designating a plurality of measurement locations on the layer such that a concentration profile of the impurity within the layer may be determined. In some embodiments, exposing the layer and substrate may include forming an oxidized interface between the layer and the semiconductor substrate. Preferably, the oxidized interface is thicker underneath portions of the layer with a lower concentration of the impurity than underneath portions of the layer with a higher concentration of the impurity.

29 Claims, 4 Drawing Sheets

METHOD AND STRUCTURE FOR DETERMINING A CONCENTRATION PROFILE OF AN IMPURITY WITHIN A SEMICONDUCTOR LAYER

BACKGROUND OF THE INVENTION

1. Field of the Invention

This invention relates to determining material composition, and more particularly to a method and a structure for determining one or more component concentrations contained in a material.

2. Description of the Related Art

The following descriptions and examples are not admitted to be prior art by virtue of their inclusion within this section.

Compositional analysis of materials is desirable for many applications. For example, the type of adhesive applied to a tape product or the type of metal or paint applied to a product for corrosion protection is critical for the functionality of the products. The method and structure described herein are discussed primarily with respect to the analysis of thin films within semiconductor devices. The term "thin film" is commonly used within the semiconductor industry when referring to layers deposited upon a semiconductor wafer during the fabrication of a transistor. Specialized materials are selected for thin films to perform specific functions of the transistor. In order for a thin film to be effective, it must conform to strict electrical, chemical, and structural requirements. Thin film materials may include, but are not limited to, metallic, semiconducting, and dielectric materials or a combination of such materials. Often, thin films are doped with impurities to heighten the effectiveness of the material used.

Inaccurate analysis of one or more process parameters within the fabrication of a semiconductor device, such as a transistor, may hinder or prohibit the function of the device, leading to a reduction in production efficiency and device quality. The characterization of thin films is especially important, since the effectiveness and reliability of thin films play an important, central role in the operation of a semiconductor device. Therefore, thin films must be accurately analyzed in order to meet a semiconductor device's functionality requirements. In addition, as production volumes and efforts to improve process control increase in the integrated circuit fabrication industry, the ability to accurately characterize semiconductor processes and the materials associated with such processes in a timely manner becomes more critical.

At present, it is difficult to find an analytical technique suitable for use in semiconductor fabrication that can characterize the composition of a thin film in a simple, accurate, and cost-effective manner. Many current techniques require large pieces of equipment, such as spectrometers that are not used within a fabrication area due to size and cleanliness requirements. Some of these techniques may include, for example, Secondary Ion Mass Spectroscopy (SIMS), Auger Electron Spectroscopy (AES), and X-ray Photoelectron Spectroscopy (XPS). In addition, current techniques typically employ expensive equipment, thereby increasing the fabrication cost of the semiconductor devices. In some cases, a manufacturer may decide to forego the additional costs of purchasing a piece of analytical equipment and send samples to an outside testing facility. Such an option requires additional time for the analysis to be conducted. Often, the amount of time required for such an outside analysis is on the order of a few days or weeks. As a result, production throughput and efficiency is sacrificed due to the increased process cycle time of the devices. Consequently, many current analysis techniques do not coincide with the desire within the semiconductor fabrication industry to increase production efficiency and improve process control.

It would, therefore, be advantageous to create a method and a structure with which to determine the composition of a material in a simple, accurate, and cost-effective manner. Such a method and structure would be particularly beneficial for determining the concentrations of an impurity within a thin film of a semiconductor device.

SUMMARY OF THE INVENTION

The problems outlined above may be in large part addressed by a method and a structure for measuring a concentration of an impurity within a layer arranged upon a semiconductor substrate. Such an impurity may include any species adapted to enhance or retard oxidation of the layer. For example, the impurity may include nitrogen, fluorine, xenon, iodine, or silicon. The method may include exposing the layer and semiconductor substrate to oxidizing conditions. In some embodiments, exposing the layer and semiconductor substrate may include forming an oxidized interface between the layer and the semiconductor substrate. Preferably, the oxidized interface is thicker underneath portions of the layer with a lower concentration of the impurity than underneath portions of the layer with a higher concentration of the impurity. The method may further include determining a difference in total dielectric thickness above the semiconductor substrate from before exposing the layer and substrate to after exposing the layer and substrate. The difference may be determined by measuring a first thickness of the layer prior to exposing the layer and substrate followed by measuring a second thickness of the layer and a thickness of the oxidized interface subsequent to exposing the layer and substrate. Subsequently, the difference may be correlated to a concentration of the impurity.

In some cases, the method may include designating a plurality of measurement locations on the layer prior to exposing the layer and semiconductor substrate to oxidizing conditions. In this manner, a concentration profile of the impurity within the layer may be determined. In addition, the method may include calculating a thickness delta of total dielectric arranged above the substrate at each of the measurement locations from before exposing the layer and substrate to after exposing the layer and substrate. The thickness delta corresponding to each of the measurement locations may then be correlated to a concentration of the impurity to form a concentration profile. In some embodiments, the concentration profile produced by the method may be a lateral concentration profile. As such, designating the measurement locations may include identifying a plurality of points on the layer having the same thickness in some embodiments. In an alternative embodiment, the concentration profile produced by the method may be a depth concentration profile. In such an embodiment, designating the measurement locations may include identifying a plurality of points on the layer, which correspond to different thickness increments of the layer. In yet another embodiment, the concentration profile produced by the method may be a lateral and depth concentration profile. In any of the embodiments, designating the measurement locations may further include identifying a subset of the plurality of points on the layer. For example, designating the measurement locations may include identifying a subset of the plurality of points located at an equal distance from the center of the semiconductor topography.

In some embodiments, the method may further include removing a portion of the layer including the measurement locations prior to exposing the layer and semiconductor substrate. In some cases, removing the portion of the layer may include forming a substantially level surface across the entirety of the layer. Alternatively, removing the portion of the layer may include forming a sloped or stepped surface across at least a portion of the layer. In such an embodiment, the thickness increments of the measurement locations may range from greater than approximately 0 angstroms to the thickness of the layer prior to removing the portion of the layer. In addition or alternatively, the thickness increments of the measurement locations, in such an embodiment, may vary incrementally by less than 20% of the thickness of the layer prior to removing the portion of the layer. In a preferred embodiment, correlating the thickness delta to the concentration of the impurity may include subtracting a concentration of the impurity within a first thickness increment of the layer from a concentration of the impurity within a second thickness increment of the layer. In such an embodiment, the second thickness increment is preferably greater than the first thickness increment.

A semiconductor topography is also contemplated herein. Such a semiconductor topography may include an oxidized interface between a semiconductor substrate and a layer comprising an impurity, wherein a thickness of the oxidized interface is dependent upon a concentration of the impurity within a respective portion of the layer. For example, in some embodiments, the first thickness of the oxidized interface may be larger than a second thickness of the oxidized interface. In such an embodiment, the concentration of the impurity within a portion of the layer corresponding to the portion of the oxidized interface with the first thickness may be larger than the concentration of the impurity within a portion of the layer corresponding to the portion of the oxidized interface with the second thickness. In some embodiments, the layer may include a sloped surface. In other embodiments, the layer may include a stepped surface. In yet another embodiment, the layer may include a substantially level surface. In some cases, the thickest portion of the layer may be approximately 100 angstroms or less. More specifically, the thickest portion of the layer may be approximately 35 angstroms or less. In either embodiment, the layer may include, for example, silicon oxynitride, silicon dioxide/silicon nitride/silicon dioxide, or fluorine doped silicon oxide.

There may be several advantages to determining the concentration of an impurity within a layer using the method and structure described herein. For example, the method and structure described herein may offer a manner with which to analyze the impurity concentration of a thin film of a semiconductor device in an accurate and timely manner. In particular, the method described herein may determine an impurity concentration of a thin film within a semiconductor fabrication area in less than approximately one hour. Such a method may be particularly advantageous over the conventional method of sending samples to an outside testing facility and waiting days or weeks for the results. As such, process cycle time may be decreased, thereby increasing production efficiency. In addition, the method described herein may advantageously reduce fabrication costs. In particular, outside testing fees and/or expensive equipment used for in-house analysis do not have to be expensed or purchased, thereby decreasing fabrication costs.

BRIEF DESCRIPTION OF THE DRAWINGS

Other objects and advantages of the invention will become apparent upon reading the following detailed description and upon reference to the accompanying drawings in which:

FIG. 4 depicts a partial cross-sectional view of the semiconductor topography in which the layer and semiconductor substrate are exposed to oxidizing conditions subsequent to the sloped surface formation of FIG. 2a;

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning to the drawings, exemplary embodiments of a method for measuring a concentration of an impurity within a layer of a semiconductor topography is shown in FIGS. 1–6. Moreover, FIGS. 1–6 illustrate a method for determining a concentration profile of an impurity within such a layer. In general, the arrangement of impurities within a material may differ. In particular, one or more portions of a layer may include higher concentrations of an impurity than other portions of the layer. The method described herein offers a technique by which to determine the concentration of an impurity within a particular location of a layer. As such, the method described herein may be used to determine the concentration profile of an impurity within a layer with a graded refractive index. In general, an impurity may refer to any species deliberately introduced into a material. In a preferred embodiment of the method described herein, the impurity may include any species adapted to enhance or retard oxidation of the material. For example, the impurity may include nitrogen, fluorine, xenon, iodine, or silicon.

Figure 1:
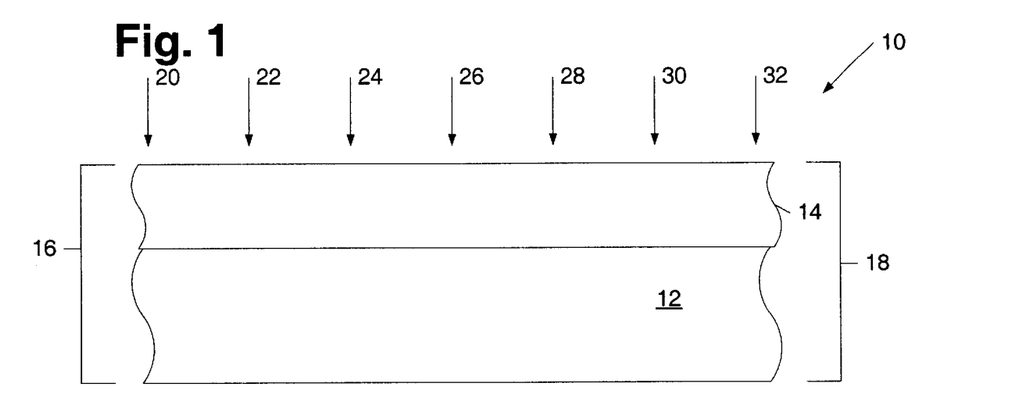
FIG. 1 depicts a partial cross-sectional view of a semiconductor topography in with a layer arranged above a semiconductor substrate.

FIG. 1 depicts a partial cross-sectional view of semiconductor topography 10 with dielectric 14 formed above semiconductor substrate 12. More specifically, FIG. 1 shows semiconductor topography 10 with dielectric 14 formed upon and in contact with semiconductor substrate 12. Semiconductor substrate 12 preferably includes silicon. As such, semiconductor substrate may be a monocrystalline silicon substrate. In other embodiments, semiconductor substrate 12 may include an epitaxial silicon layer grown on a monocrystalline silicon substrate or a silicon on insulator (SOI) layer formed upon a monocrystalline substrate. In addition or alternatively, semiconductor substrate 12 may be doped either n-type or p-type. Dielectric 14 may include any of various dielectric materials containing silicon, oxygen, and/or one or more impurity species. For example, dielectric 14 may include silicon-rich oxide, nitrided silicon dioxide, silicon oxynitride, fluorine-doped silicon dioxide, xenon-doped silicon dioxide, iodine-doped silicon dioxide, or any combination of such materials. Dielectric 14 is preferably a thin film and therefore, may have a thickness between approximately 30 angstroms and approximately 100 angstroms. However, larger or smaller thicknesses of dielectric 14 may be appropriate depending on the process conditions of the method described herein.

Figure 2A:
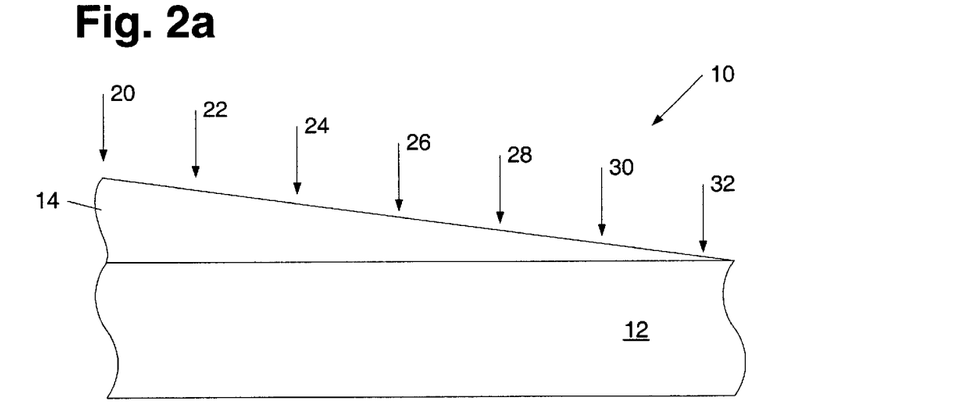
FIG. 2a depicts a partial cross-sectional view of the semiconductor topography in which a portion of the layer of FIG. 1 is removed to form a sloped surface.
Figure 2B:
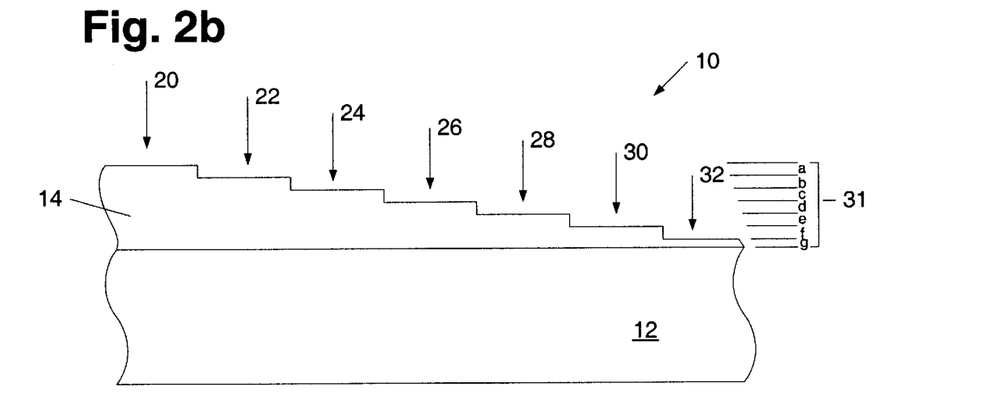
FIG. 2b depicts a partial cross-sectional view of the semiconductor topography, in an alternative embodiment, in which a portion of the layer of FIG. 1 is removed to form a stepped surface.
Figure 2C:
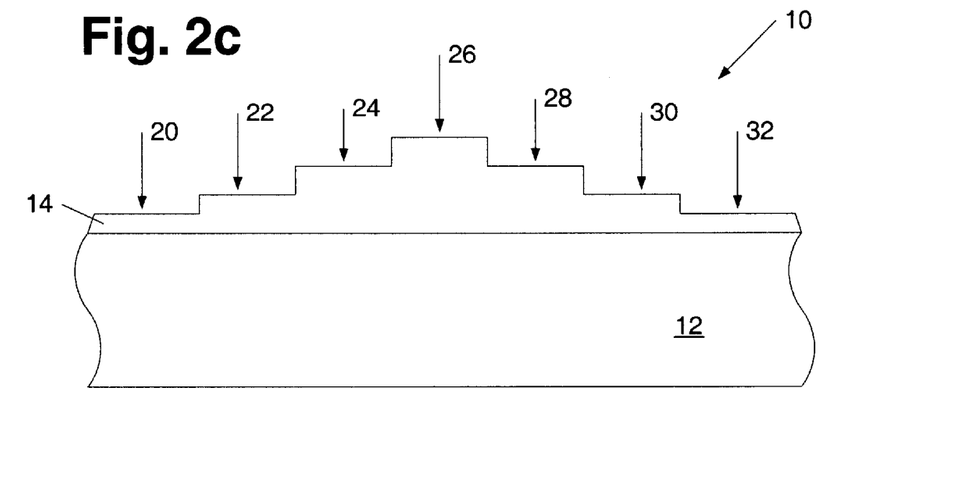
FIG. 2c depicts a partial cross-sectional view of the semiconductor topography, in an alternative embodiment, in which a portion of the layer of FIG. 1 is removed to form a different stepped surface.

FIGS. 2a–2c illustrate the removal of a portion of dielectric 14 across semiconductor topography 10. In particular, FIG. 2a illustrates the removal of a portion of dielectric 14 such that a sloped surface is formed. In contrast, FIG. 2b illustrates the removal of a portion of dielectric 14 such that a stepped surface is formed. In either embodiment, the removal of dielectric 14 may be particularly advantageous for determining a depth concentration profile of an impurity within dielectric 14. On the other hand, FIG. 2c shows an alternative embodiment, in which a stepped surface of a different configuration is formed within dielectric 14. Such an alternative configuration may be particularly advantageous for compiling a combination concentration profile, detailing both lateral and depth concentration variations of an impurity within dielectric 14. More specifically, the configuration of FIG. 2c may allow a depth concentration profile on both sides of measurement location 26 to be determined, thereby allowing portions of dielectric 14 to be laterally compared.

In yet another embodiment (not shown), a portion of dielectric 14 may be removed such that a substantially level surface is formed, i.e., an upper portion of dielectric 14 comprising a substantially uniform thickness may be removed to form an upper surface similar to that of FIG. 1. Such a removal of dielectric 14 may be particularly advantageous for determining a lateral concentration profile of an impurity at a specific depth within dielectric 14. In any of the embodiments, lateral surfaces 16 and 18 of semiconductor topography 10 are drawn to indicate the continuation of semiconductor topography 10 across a semiconductor wafer. As such, the removal of portions of dielectric 14, in some embodiments, may only be across a portion of a wafer. In other embodiments, however, lateral surfaces 16 and 18 of semiconductor topography 10 may indicate the outer edge of a semiconductor wafer: In such an embodiment, the removal of portions of dielectric 14 may extend across an entire wafer.

The removal of portions of dielectric 14 may be conducted in a variety of manners. For example, portions of dielectric 14 may be patterned by a photolithography process to subsequently form a stepped surface. In an alternative embodiment, dielectric 14 may be etched to form a substantially level or sloped surface. In either embodiment, the removal of portions of dielectric 14 may include using either wet or dry etch techniques. For example, in one embodiment, a semiconductor wafer comprising semiconductor topography 10 may be exposed to a wet etch chemistry such that a sloped surface may be obtained. Such a method may include positioning lateral surface 18 in the chemistry and gradually moving the remainder of the wafer such that lateral surface 16 is the last portion of the wafer to be submerged in the chemistry. The method may further continue by removing the wafer from the chemistry along the path of entry. In this manner, the portion of dielectric 14 arranged between lateral surfaces 16 and 18 may be graded or sloped, since the portions of dielectric 14 arranged adjacent to lateral surface 18 may be etched progressively longer than the portions of dielectric 14 arranged adjacent to lateral surface 16. Several other methods known to those in semiconductor fabrication for removing portions of a dielectric material may be performed to obtain a desired cross-sectional profile of dielectric 14. As such, the methods for removal of portions of dielectric 14 are not restricted to the methods described herein for removing portions of dielectric 14.

In general, any of the structures of FIGS. 1–2c may be used in the method described herein for measuring the concentration of an impurity within dielectric 14. Likewise, any of the structures of FIGS. 1–2c may be used to determine a concentration profile of an impurity within dielectric 14. In particular, configurations with a substantially level surface, such as that of FIG. 1, may be used to determine a lateral concentration profile of an impurity within dielectric 14, while FIGS. 2a–2c may be used to determine depth or combination concentration profiles of an impurity within dielectric 14 as noted above. In addition, several other structures with alternative configurations of dielectric 14 may be used in the method described herein. For example, a structure with a dielectric layer with opposing sloped surfaces similar to the opposing stepped surfaces of FIG. 2c may be used. In addition, a structure with a portion of dielectric 14 removed but comprising a substantially level surface may be used. Furthermore, the surface configuration of dielectric 14 need not be symmetrical or uniform in order for it to be used in the method described herein. In this manner, the surface configuration of dielectric 14 may include a variety of stepped surface configurations disproportionate from each other. In addition or alternatively, the surface configuration may include a variety of sloped surfaces of different angles and lengths. As such, the configurations of dielectric 14 illustrated in FIGS. 1–2c are shown as exemplary embodiments and are not to be construed as the only configurations available for use in the method described herein.

As shown in FIGS. 1–2c, measurement locations 20–32 may be designated across semiconductor topography 10 and more specifically upon dielectric 14. Such a designation of measurement points may be performed before or after the removal of portions of dielectric 14. In general, the measurement points may be located with respect to various references, such as wafer flats or alignments marks formed on the substrate. In an embodiment in which a lateral concentration profile is to be determined, designating measurement locations 20–32 may include identifying a plurality of points on dielectric 14 having substantially the same thickness as shown in FIG. 1. In an embodiment in which a depth concentration profile is to be determined, designating measurement locations 20–32 may include identifying a plurality of points corresponding to different thickness increments of dielectric 14 as shown in FIGS. 2a–2c. In this manner, each of the measurement locations may represent a different thickness increment of the dielectric.

The thickness increments of the dielectric may refer to distinct sublayers of the dielectric. An illustration of such thickness increments may be most easily illustrated in FIG. 2b with the stepped surface of dielectric 12. In particular, thickness increments 31a–31g are shown relative to the stepped surface of dielectric 14. As such, thickness increment 31a may represent an uppermost portion of dielectric 14 residing above thickness increment 31b and thickness increment 31g may represent a lowermost portion of dielectric 14 residing below thickness increment 31f. Thickness increments 31b–31g may individually represent sublayers of dielectric 14 interposed between respective overlying and underlying thickness increments. Although thickness increments 31a–31g are shown relative to the stepped surface of dielectric 14 in FIG. 2b, such an assignment of thickness increments may be applied to the sloped surfaces of FIGS. 2a and 4 as well. In addition, although thickness increments 31a–31g are shown in sequential order of thickness, the upper surface of dielectric 14 may vary such that thickness increments 31a–31g are not incrementally aligned. For example, dielectric 14 in the embodiment of FIG. 2c may include thickness increments of varying depths on either side of semiconductor topography 10.

As shown in FIGS. 2c, dielectric 14 may be divided into several thickness increments. In some embodiments, the number of thickness increments may correspond to the number of measurement locations designated upon dielectric 14. For example, in the embodiments of FIGS. 1–3, dielectric 14 may include seven distinct thickness increments. Fewer or more thickness increments, however, may be included depending on the intricacy of the desired concentration profile. For example, more than one measurement point may be designated per thickness increment. In this manner, a greater number of measurement points than thickness increments may be designated across the topography. In particular, one or more of thickness increments 31a–31g may include a plurality of measurement points. In other embodiments, fewer measurement points than thickness increments may be designated across a topography. For example, in an embodiment in which a stepped surface is formed, each thickness increment of the stepped surface may not include a measurement point. In a preferred embodiment, however, at least one measurement location is designated for each thickness increment defined by the stepped surface.

In a preferred embodiment, the measurement locations may vary uniformly across the dielectric. In other words, the measurement locations may be evenly spaced across the semiconductor topography. In this manner, the thickness increments corresponding to each of the measurement locations may be substantially the same. As such, the thickness of each thickness increment may depend on the number measurement locations designated. For example, in an embodiment in which seven measurement locations are designated along a dielectric, each thickness increment may be approximately 14% of the total thickness of the original dielectric layer. Smaller or greater thickness increments may be used, however, depending on the intricacy of the desired concentration profile. In a preferred embodiment, each of the thickness increments may be less than approximately 20% of the total thickness of the original dielectric layer. Consequently, in an embodiment in which the thickness increments are substantially equal, the thickness increments may vary incrementally by less than approximately 20% of the thickness of the original dielectric layer.

In an alternative embodiment, the thickness increments may be substantially unequal. In this manner, each of the thickness increments may not have the same thickness. Embodiments with such unequal thickness increments may occur if measurement locations 20–32 are designated at an unequal distance from each other along sloped surface of dielectric 14 in FIG. 2a, for example. In another embodiment, unequal thickness increments may be obtained if stepped portions of dielectric 14 in FIG. 2b are dissimilar in thickness. In either embodiment, the thickness increments may range from greater than approximately 0 angstroms to the thickness of dielectric 14 prior to removing the upper portion of dielectric 14 to form the sloped or stepped surfaces. Narrower ranges of thickness increments, however, may be appropriate depending on the desired concentration profile. In some embodiments, the thickness increments may vary by less than 20% of the thickness of the layer prior to removing the dielectric to form a sloped or stepped surface.

Figure 3:
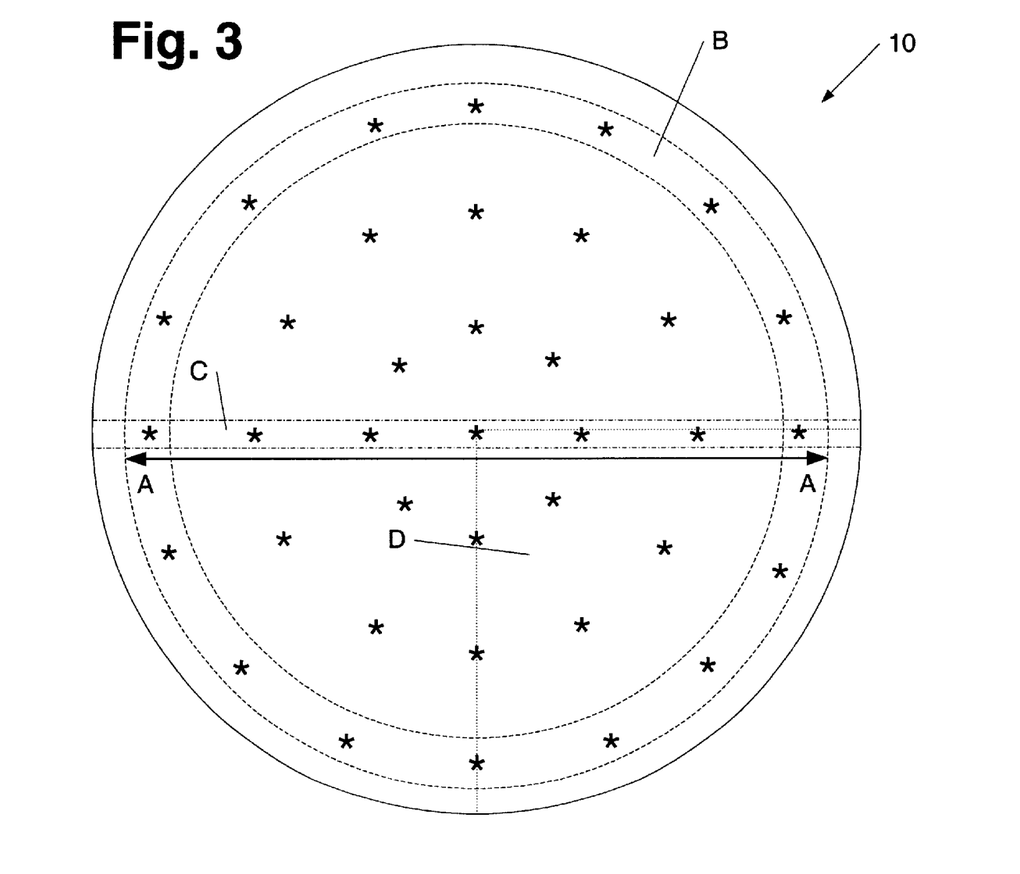
FIG. 3 depicts a top view of the semiconductor topography of FIG. 1, 2a, 2b, or 2c with a plurality of measurement points.

Although FIGS. 1–2c show seven measurement locations, any number of measurement locations may be used depending on the intricacy of the desired concentration profile. In particular, additional measurement locations may be included along semiconductor topography 10. In other embodiments, less than seven measurement locations may be designated across semiconductor topography 10. In addition or alternatively, a plurality of measurement points other than measurement locations 20–32 may be designated across semiconductor topography 10 as illustrated in FIG. 3. FIG. 3 is a top view of a wafer comprising semiconductor topography 10. The cross sectional views of semiconductor 10 in FIGS. 1–2c are taken along line A—A of FIG. 3. In addition, the measurement locations may be designated symmetrically upon dielectric 14 as shown in FIGS. 1–2c. Alternatively, the measurement locations may be designated asymmetrically upon dielectric 14.

In either embodiment, designating measurement locations may include identifying subsets of the plurality of measurement points designated across semiconductor topography 10. Designating a subset of measurement points may advantageously allow variations of impurity concentrations within certain regions of the wafer to be analyzed. Examples of such subsets (i.e, subsets B, C, and D) are outlined in FIG. 3 by dotted lines. Subset B, for example, may include a subset of points located at an equal distance from the center of the wafer. In particular, subset B may represent a plurality of measurement points designated along the outer edge of the wafer as shown in FIG. 3. A similar circular set of measurement points may be designated near the center of the wafer or in between the center and outer edge of the wafer as illustrated in FIG. 3.

Subset C, on the other hand, may include a subset of points located along a strip of semiconductor topography 10 extending from opposite edges of the wafer. For example, subset C may represent a plurality of measurement points designated along a center strip of the wafer as shown in FIG. 3. A similar set of measurement points may be designated along an off-centered strip of the wafer. In contrast, subset D may include, for example, a subset of points located within a quadrant of semiconductor topography 10 as shown in FIG. 3. In general, several regions of the wafer, including smaller and larger regions and regions of more or fewer measurement points than those referenced in subsets B, C, and D, may be designated as subsets of measurement points. Alternatively or in addition, a plurality of randomly designated points may be designated as a subset. Accordingly, the arrangement of measurement points and subsets illustrated in FIG. 3 are shown as exemplary embodiments and are not to be construed as the only subset configurations available for use in the method described herein.

Figure 4:
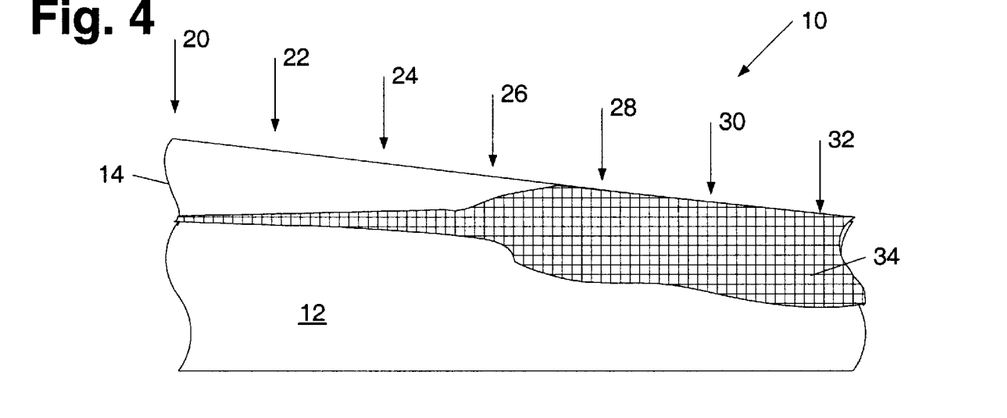

FIG. 4 illustrates a partial cross sectional view of semiconductor topography 10 of FIG. 2a (i.e., semiconductor topography 10 with the sloped surface) subsequent to its exposure to oxidizing conditions. Such an oxidation process may form oxidized interface 34 between dielectric 14 and semiconductor substrate 12. More specifically, such an oxidation process may oxidize portions of dielectric 14 and semiconductor substrate 12 to form oxidized interface 34. In general, the oxidizing conditions may oxidize twice as much of semiconductor substrate 12 as dielectric 14 as illustrated in FIG. 4. In other embodiments, topographies including a substantially level surface as in FIG. 1 or a stepped surface as in FIGS. 2b and 2c may be exposed to oxidizing conditions to form an oxidized interface between dielectric 14 and semiconductor substrate 12. Such an oxidized interface may be similar to that of oxidized interface 34 of FIG. 4 or substantially different from oxidized interface 34, depending on the surface configuration of dielectric 14. More specifically, the oxidized interface generated from the topography of FIG. 2b may be substantially similar to oxidized interface 34 of FIG. 4. In contrast, the oxidized interface generated from the topographies of FIG. 1 and 2c may be substantially different from oxidized interface 34 of FIG. 4.

In addition, the concentration of an impurity within dielectric 14 may influence the amount of oxidation that may occur with a layer, and therefore may affect the thickness of oxidized interface 34. For example, nitrogen generally blocks the diffusion of oxygen. In particular, the higher the concentration of nitrogen contained with a layer, the less the diffusion of oxygen through the layer during an oxidization process. Since the concentration of an impurity may vary laterally and vertically within a layer, the thickness of an oxidized interface may vary as shown in FIG. 4. In addition, oxygen generally diffuses in a substantially straight path such that the thickness of an oxidized interface may represent the amount of oxygen diffused through a layer for a given portion of that layer. Consequently, the thickness of a portion of an oxidized interface may relate to the concentration of an impurity contained within a respective portion of an overlying layer. "Respective" portions of overlying and underlying layers may refer to portions of the layers laterally bound and directly aligned with each other.

As such, a high concentration of nitrogen contained within a portion of dielectric 14 may produce an oxidized interface with a smaller thickness than an oxidized interface produced by oxidizing a portion of dielectric 14 containing a low concentration of nitrogen. Consequently, the concentration of an impurity at a particular measurement location within dielectric 14 may be determined by calculating the thickness delta of total dielectric residing above semiconductor substrate 12 from before exposing semiconductor topography 10 to oxidizing conditions to after exposing semiconductor topography 10 to oxidizing conditions. The reference of total dielectric residing above semiconductor substrate 12 preferably includes that of oxidized interface 34 and dielectric 14.

Figure 5:
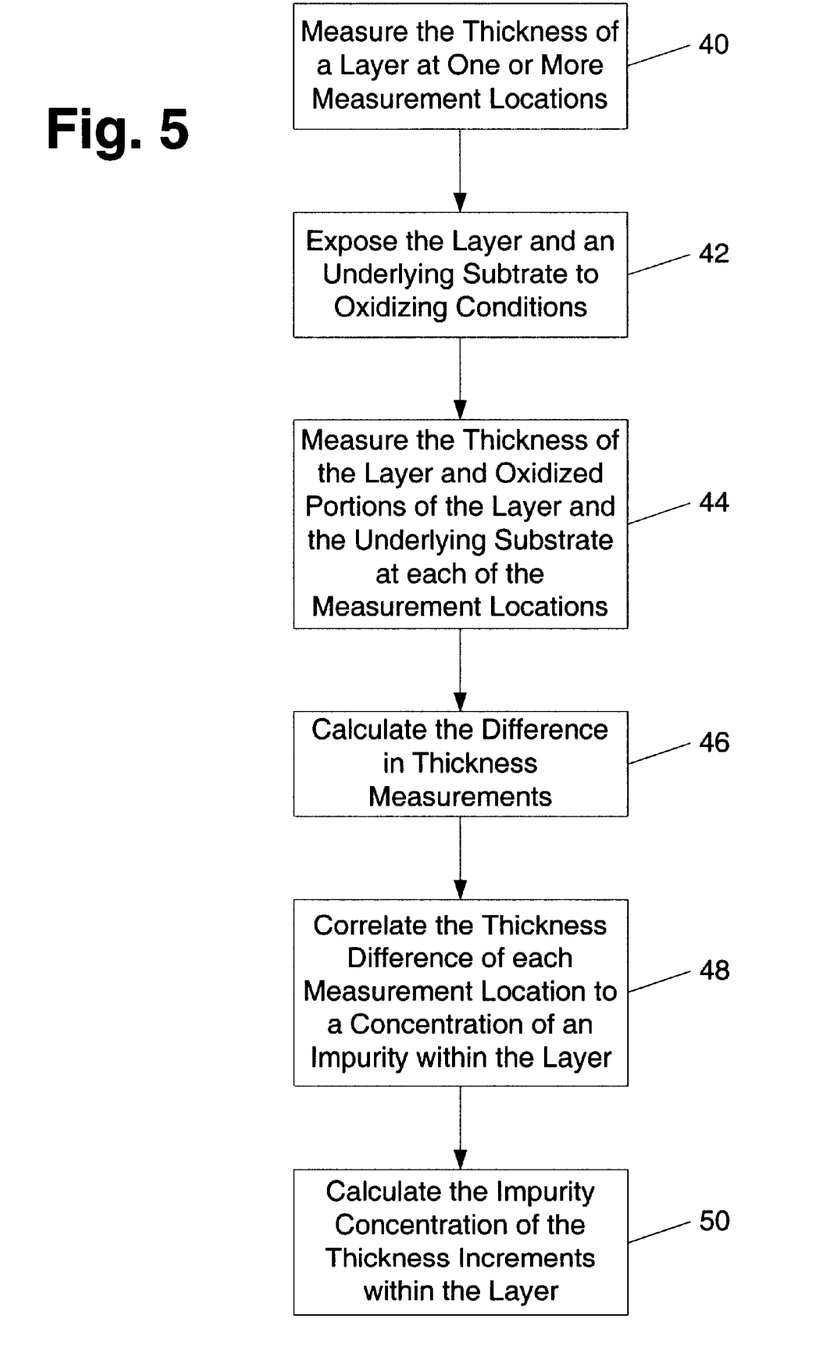
FIG. 5 depicts a flowchart of a method for measuring the impurity concentration of a material.

A flow chart of the method described herein is illustrated in FIG. 5. In particular, the method may include step 40, which includes measuring the thickness of a layer at one or more measurement locations. Such a step may be conducted after designating measurement locations and/or removing an upper portion of the layer as described in FIGS. 1–3. The thickness of the layer may be prepared in a variety of manners known in the semiconductor fabrication industry. For example, the thickness of the layer may be determined by standard optical techniques, such as ellipsometry. The method may further include step 42, which involves exposing the semiconductor topography comprising the layer to oxidizing conditions. More specifically, step 42 includes exposing the layer and underlying substrate to oxidizing conditions. The method may further include step 44 for measuring the thickness of the layer and oxidized portions of the layer and underlying semiconductor substrate at each of the measurement locations after exposing the semiconductor topography to oxidizing conditions. Consequently, the difference in thickness measurements or the thickness delta of the dielectric residing above the semiconductor substrate may be determined as indicated in step 46. In a preferred embodiment, the thickness of the layer and oxidized portions of the layer and underlying semiconductor substrate may be measured by the same method as used for measuring the thickness of the layer prior to oxidation.

As stated above, the thickness delta of the dielectric residing above a semiconductor substrate may be correlated to a concentration of an impurity in layer arranged above the substrate. As such, the method may further include correlation step 48 following step 46. Such a correlation step may be conducted with the use of calibration data. The calibration data may be prepared in a variety of manners known in the semiconductor fabrication industry. For example, the calibration data may be contrived from SIMS analysis of a plurality of samples with known impurity concentrations. In addition, the calibration data may be representative of particular deposition techniques. For instance, different calibration data may be needed to differentiate between Rapid Thermal Oxidation (RTO) deposited nitrogen oxides and furnace grown nitrided oxides.

Upon correlating the thickness delta of each measurement location, the concentration of the impurity within the respective thickness increment of the layer may be determined as shown in step 50. In this manner, a concentration profile of the impurity within the layer may be determined. Step 50 may involve subtracting the impurity concentration of a measurement location corresponding to a lower thickness increment from the impurity concentration of the measurement location corresponding the thickness increment being calculated. For example, in the embodiment of FIG. 2b, the impurity concentration within thickness increment 31c may be calculated by subtracting the correlated impurity concentration of measurement location 26 from the correlated impurity concentration of measurement location 24. More specifically, in an embodiment in which, the correlated impurity concentration of measurement location 26 is approximately $125.72 \times 10^{13}$ cm$^{-3}$ and the correlated impurity concentration of measurement location 28 is approximately $68.36 \times 10^{13}$ cm$^{-3}$, thickness increment 31d may include an impurity concentration of approximately $57.36 \times 10^{13}$ cm$^{-3}$.

Figure 6:
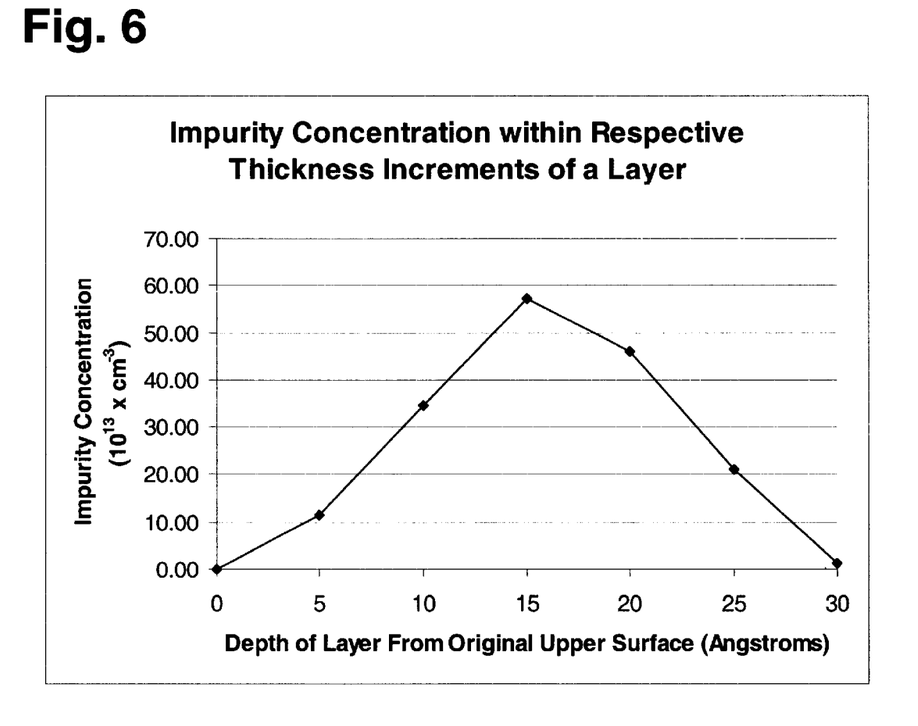
FIG. 6 depicts an impurity concentration profile of a layer with respect to thickness increments of the layer.

Preferably, the calculated impurity concentration corresponding to each of the thickness increments may be plotted to show the distribution of the impurity within the layer. An example of such a concentration profile is illustrated in FIG. 6 using the data of Table 1 below. Table 1 includes a first column detailing the amount of dielectric removed respective to an original upper surface of the dielectric. The second column of Table 1 outlines the thickness of the dielectric subsequent to the removal of upper portions of the dielectric, but prior to the oxidation process. As shown in Table 1, the original thickness of the dielectric is approximately 32 angstroms and thickness increments of approximately 5 angstroms are designated through the layer. Larger or smaller thickness increments and layers, however, may be used for the method described herein. The third column of Table 1 lists the thickness of total dielectric residing above the substrate after the oxidation process, while the fourth column yields the thickness delta between the values of the second and third columns. The last two columns list the impurity concentration relative to the calculated thickness delta of the fourth column and the impurity concentration corresponding to the respective thickness increment, respectively.

The plot of FIG. 6 illustrates the impurity concentration at the corresponding depth of each thickness increment with respect to the layer's original upper surface. As such, the plot of FIG. 6 may include the values of the last column of Table 1 versus the amount of dielectric removed prior to oxidation as listed in the first column of Table 1. As shown in FIG. 6, the highest concentration of the impurity within the dielectric layer is located approximately 15 angstroms from the original upper surface of the dielectric layer. In addition, the upper and lower most surfaces of the dielectric layer include little or no concentration of the impurity. Such a configuration profile may be indicative of a Rapid Thermal Oxidation (RTO) deposited nitrogen oxide, in an embodiment in which the impurity includes nitrogen. It is noted that FIG. 6 is merely illustrated an example concentration profile. Several other concentration profiles may exist depending on the deposition process parameters and the impurities contained within the dielectric layer. For example, a concentration profile which may be indicative of a furnace grown nitrided oxide may include a high concentration of nitrogen near the lowermost surface of the dielectric and a substantially lower, but constant impurity concentration in the upper half of the dielectric.

TABLE 1

| Amount of Dielectric Removed Prior to Oxidation (Angstroms) | Thickness of Dielectric Prior to Oxidation (Angstroms) | Thickness of Dielectric above the Substrate after Oxidation (Angstroms) | Thickness Delta (Angstroms) | Impurity Concentration ($10^{13}$ cm$^{-3}$) | Impurity Concentration within Respective Thickness Increment ($10^{13}$ cm$^{-3}$) |
|---|---|---|---|---|---|
| 0 | 32 | 35 | 3 | 171.61 | 0.00 |
| 5 | 27 | 30 | 3 | 171.61 | 11.47 |
| 10 | 22 | 28 | 6 | 160.14 | 34.42 |
| 15 | 17 | 32 | 15 | 125.72 | 57.36 |
| 20 | 12 | 42 | 30 | 68.36 | 45.89 |
| 25 | 7 | 49 | 42 | 22.47 | 21.03 |
| 30 | 2 | 49.5 | 47.5 | 1.44 | 1.44 |

It will be appreciated to those skilled in the art having the benefit of this that this invention is believed to provide a method and a system for processing a semiconductor topography. Further modifications and alternative embodiments of various aspects of the invention will be apparent to those skilled in the art in view of this description. For example, the method described herein could be used to determine the concentration or concentration profile of a variety of impurities, which impact the growth of oxidation. Furthermore, any number of measurement locations and thickness increments may be designated for a given topography depending on the intricacy of the desired concentration profile. It is intended that the following claims be interpreted to embrace all such modifications and changes and, accordingly, the drawings and the specification are to be regarded in an illustrative rather than a restrictive sense.

What is claimed is:

1. A method for measuring concentration of an known impurity within a dielectric layer arranged upon a semiconductor substrate, comprising:
   exposing the dielectric layer and semiconductor substrate to oxidizing conditions;
   determining a difference, from before said exposing to after said exposing, in total dielectric thickness above the semiconductor substrate; and
   correlating the difference to a concentration of the impurity.

2. The method of claim 1, wherein said exposing comprises forming an oxidized interface between the dielectric layer and the semiconductor substrate, and wherein said oxidized interface is thicker underneath portions of the dielectric layer comprising a lower concentration of the impurity than underneath portions of the dielectric layer comprising a higher concentration of the impurity.

3. The method of claim 2, wherein said determining comprises:
   measuring a first thickness of the dielectric layer prior to said exposing; and
   measuring a second thickness of the dielectric layer and a thickness of the oxidized interface subsequent to said exposing.

4. The method of claim 1, wherein said impurity comprises a species adapted to retard the oxidation of the dielectric layer.

5. The method of claim 1, wherein said impurity comprises a species adapted to enhance the oxidation of the dielectric layer.

6. The method of claim 1, wherein said impurity is a species selected from a group consisting of nitrogen, fluorine, iodine, xenon, and silicon.

7. A method for determining a concentration profile of a known component within a layer arranged upon a semiconductor substrate, comprising:
   designating a plurality of measurement locations on the layer;
   exposing the layer and the semiconductor substrate to oxidizing conditions;
   calculating a thickness delta of total dielectric arranged above the substrate from before said exposing to after said exposing at each of the measurement locations; and
   correlating the thickness delta corresponding to each of the measurement locations to a concentration of the impurity.

8. The method of claim 7, wherein said concentration profile is a lateral concentration profile.

9. The method of claim 8, wherein said designating the measurement locations comprises identifying a plurality of points having the same thickness.

10. The method of claim 7, wherein said concentration profile is a depth concentration profile.

11. The method of claim 10, further comprising removing a portion of the layer comprising the measurement locations prior to said exposing.

12. The method of claim 11, wherein said removing comprises forming a sloped surface across a portion of the layer.

13. The method of claim 11, wherein said removing comprises forming a stepped surface across a portion of the layer.

14. The method of claim 11, wherein said designating the measurement locations comprises identifying a plurality of points on the layer which correspond to different thickness increments of the layer subsequent to said removing.

15. The method of claim 14, wherein designating further comprises identifying a subset of the plurality of points located at an equal distance from the center of the semiconductor topography.

16. The method of claim 14, wherein said thickness increments range from greater than approximately 0 angstroms to the thickness of the layer prior to said removing.

17. The method of claim 14, wherein said thickness increments vary incrementally by less than approximately 20% of the thickness of the layer prior to said removing.

18. The method of claim 14, wherein said correlating comprises subtracting a concentration of the impurity within a first thickness increment of the layer from a concentration of the impurity within a second thickness increment of the layer, wherein the second thickness increment is greater than the first thickness increment.

19. A semiconductor topography, comprising an oxidized interface between a semiconductor substrate and a layer comprising an impurity, wherein a thickness of the oxidized interface is dependent upon a concentration of the impurity within a respective portion of the layer.

20. The semiconductor topography of claim 19, wherein the layer comprises a sloped surface.

21. The semiconductor topography of claim 19, wherein the layer comprises a stepped surface.

22. The semiconductor topography of claim 19, wherein a first thickness of the oxidized interface is larger than a second thickness of the oxidized interface, and wherein the concentration of the impurity within a portion of the layer corresponding to a portion of the oxidized interface with the first thickness is larger than the concentration of the impurity within a portion of the layer corresponding to a portion of the oxidized interface with the second thickness.

23. The semiconductor topography of claim 19, wherein said layer comprises silicon oxynitride.

24. The semiconductor topography of claim 19, wherein said layer comprises silicon dioxide/silicon nitride/silicon dioxide.

25. The semiconductor topography of claim 19, wherein said layer comprises fluorine doped silicon oxide.

26. The semiconductor topography of claim 19, wherein the thickest portion of the layer is approximately 100 angstroms or less.

27. The semiconductor topography of claim 19, wherein the thickest portion of the layer is approximately 35 angstroms or less.

28. The method of claim 1, further comprising removing a portion of the dielectric layer prior to said exposing.

29. The method of claim 1, wherein said correlating comprises subtracting a concentration of the impurity within a first thickness increment of the dielectric layer from a concentration of the impurity within a second thickness increment of the dielectric layer, wherein the second thickness increment is greater than the first thickness increment.

* * * * *

UNITED STATES PATENT AND TRADEMARK OFFICE
CERTIFICATE OF CORRECTION

PATENT NO. : 6,664,120 B1
DATED : December 16, 2003
INVENTOR(S) : Narayanan et al.

It is certified that error appears in the above-identified patent and that said Letters Patent is hereby corrected as shown below:

Column 11,
Line 57, please delete "concentration of an known" and substitute therefor
-- concentration of a known --.

Signed and Sealed this

Thirteenth Day of April, 2004

JON W. DUDAS
*Acting Director of the United States Patent and Trademark Office*